United States Patent
Clikeman et al.

[11] Patent Number: 5,972,363
[45] Date of Patent: Oct. 26, 1999

[54] USE OF AN ENCAPSULATED BIOACTIVE COMPOSITION

[75] Inventors: Richard Roy Clikeman, Morrisville; John Natoli, Ambler; Morris Christopher Wills, Philadelphia; Yili Guo, Maple Glen, all of Pa.

[73] Assignee: Rohm and Haas Company, Philadelphia, Pa.

[21] Appl. No.: 09/013,625

[22] Filed: Jan. 26, 1998

Related U.S. Application Data

[60] Provisional application No. 60/043,844, Apr. 11, 1997.
[51] Int. Cl.[6] .................................................. A01N 25/28
[52] U.S. Cl. ........................ 424/408; 424/405; 424/406; 424/419; 427/213.36; 428/402.21; 264/4.1
[58] Field of Search ..................... 424/405, 406, 424/408, 419, 497; 427/213.36, 213.34; 428/402.21, 402.22; 264/4.1

[56] References Cited

U.S. PATENT DOCUMENTS

| | | |
|---|---|---|
| 4,186,120 | 1/1980 | Ugelstad . |
| 4,336,173 | 6/1982 | Ugelstad . |
| 4,722,838 | 2/1988 | Tocker ..................................... 424/408 |
| 5,147,937 | 9/1992 | Frazza et al. . |
| 5,237,004 | 8/1993 | Wu et al. . |
| 5,346,954 | 9/1994 | Wu et al. . |
| 5,521,266 | 5/1996 | Lau . |
| 5,674,519 | 10/1997 | Curtis et al. ............................. 424/408 |

FOREIGN PATENT DOCUMENTS 0203724  12/1986  European Pat. Off. .

OTHER PUBLICATIONS

"Preparation of Nonspherical, Monodisperse Polymer Particles and Their Self–Organization", A. T. Skjeltorp, J. Ugelstad, T. Ellingsen, Journal of Colloid and Interface Seience, vol. 113, No. 2, pp. 577–582, Oct. 1986.

"Advances in Colloid and Interface Science", J. Ugelstad. P. C. Mark, 13, 101–140 (1980).

"New Developments in Production and Application of Monosized Polymer Particles". J. Ugelstad, T. Ellingsen, A. Berge, Polym Matur Sci Eng, 54, pp. 521–525, 1986.

*Primary Examiner*—Neil S. Levy
*Attorney, Agent, or Firm*—Thomas D. Rogerson

[57] ABSTRACT

The present invention relates to a method for delivering a bioactive compound to the site where it will exhibit its biological affect and controlling the delivery of the bioactive compound through the physical-chemical properties of a particle containing the bioactive compound. The method is particularly useful for delivering agricultural chemicals and pharmaceutical compounds.

8 Claims, No Drawings

USE OF AN ENCAPSULATED BIOACTIVE COMPOSITION

This application claims benefit Provisional Application 60/043,844, filed Apr. 11, 1997.

The present invention relates to a method for delivering a bioactive compound to the site where it will exhibit its biological effect and controlling the delivery of the bioactive compound through the physical-chemical properties of a particle containing the bioactive compound. The method is particularly useful for delivering agricultural chemicals and pharmaceutical compounds.

One of the major difficulties encountered when using bioactive compounds is to deliver the compound to its site of action in as efficient a manner as possible. One method, which has been found useful, is to encapsulate the compound inside another material, which serves to protect the compound, and then apply the encapsulated compound to its site of action. However, there are two significant problems associated with encapsulating a bioactive compound. First, many compounds are incompatible with typical encapsulation processes. Second, it is difficult, often impossible, to control the release of the compound from the encapsulating material. This lack of control may be the result of many different factors such as, for example, the chemical properties of the encapsulating material or the variation in particle size of the capsules.

U.S. patent application Ser. No. 08/704,316, filed Sep. 19, 1996, discloses a method for forming, in an aqueous medium, particles containing liquid crystal domains in which the particles have a narrower particle size distribution than particles formed by conventional means. The particles may be viewed as comprising a core containing the liquid crystal surrounded by a polymer shell. The liquid crystal may be replaced by a number of different materials, including bioactive compounds. We have discovered that by manipulating the components making up the core and the polymer shell, that the method disclosed in Ser. No. 08/704,316 can be used to produce encapsulated bioactive compounds in which the release of the bioactive compound may be controlled. Because of the controlled release obtained, the efficacy of the bioactive compound may be improved. In addition, the use of a properly constructed encapsulated bioactive material may allow delivery of the bioactive compound to its site of action in a manner not previously possible. In addition to these benefits, encapsulation often may result in reducing undesirable properties of a bioactive compound, such as, for example, excessive volatility, formulation instability, phytotoxicity, exposure to humans, and the like.

This invention is a method for administering a bioactive material, comprising: delivering to a target or the locus of the target a polymer encapsulated bioactive material comprising a polymer and a bioactive material, wherein:
  i) the polymer encapsulated bioactive material has a particle size in the range of from 0.1 to 15 microns;
  ii) the polymer encapsulated bioactive material has a particle size distribution of from 1.0 to 1.5; and
  iii) the polymer shell is not permeable to the bioactive material under ambient conditions and is at least partially permeable to the bioactive material at a target.

The term "administering" means providing a quantity of bioactive material to a target or to the locus of the target. The term "bioactive material" means one or more organic compounds which cause a biological effect to occur when the material comes into contact with a target site in or on a living organism. Examples of bioactive materials include, for example, human and veterinary pharmaceuticals, disinfectants, pesticides, biocides, marine anti-fouling agents, and the like. The term "delivery" or "delivering" means bringing the polymer encapsulated bioactive material into contact with the target or within the locus of the target such that when the bioactive material is released it will cause a biological effect to occur. The term "target" means the object or site where the bioactive material causes its effect. Targets may include, for example; intact organisms such as a caterpillar, a fungal cell, or a weed; a tissue or organ such as a cell wall, a plant root, or an animal vascular system; an enzyme such as cholinesterase, or a biological process such as photosynthesis, nerve conduction, gene replication or transcription, or cellular active transport. The term "locus of the target" means the environment in which the target is found or an environment in which the bioactive compound may be released such that it subsequently comes into contact with the target. Examples of such loci include, for example, soil if the target is a soil dwelling pest such as a fungus, an animal stomach if the target is a biological process in which the bioactive compound is absorbed through the stomach to reach its site of action, or a leaf if the target is a leaf-chewing pest. The term "ambient conditions" means the environmental conditions in which the polymer encapsulated bioactive material is manufactured, stored, or applied. For purposes of this invention, ambient conditions are any conditions under which release of the bioactive material would be undesirable. The term "not permeable" means that under ambient conditions there is zero or only minimal release of bioactive material from the particle. For convenience this means that formulations of the polymer encapsulated bioactive material would be considered stable under conditions of storage and transport.

The bioactive material may be any organic material which is a liquid under the polymer swelling conditions used in the process of encapsulating the bioactive material. Preferably, the bioactive material has a low water solubility, that is, less than 50 parts per million (ppm). The material may also be a solution of a material which is normally a solid at room temperature. Examples include pesticides such as biocides, herbicides, mildewicides, insecticides and fungicides; fertilizing agents; marine anti-fouling agents; pharmaceutically active agents; and the like. The organic liquids used in this manner according to the present invention may be pure liquids, mixtures, or solutions of solid or liquid species in organic solvents.

An important aspect of the present invention is that the particles of encapsulated bioactive compound are of uniform size and in the range from 0.1 to 15 microns, preferably 0.25 to 3 microns. Uniform size results in consistent and uniform release of the bioactive compound from the encapsulating material. This further results in a predictable and consistent biological effect being produced. Particle size distribution (PD) as used herein is calculated from the weight average size, $d_w$, and the number average size, $d_n$, by the formulae:

$$PD = (d_w)/(d_n).$$

$$d_n = \Sigma n_i d_i / \Sigma n_i$$

$$d_w = \Sigma n_i d_i d_i / \Sigma n_i d_i$$

where $n_i$ is the number of domains having the particle size $d_i$. For purposes of this invention, the particle size distribution is from 1.0 to 1.5. Preferably, it is between 1.0 and 1.3. More preferably, the particle size distribution will be between 1.0 and 1.1; most preferably between 1.0 and 1.01.

The polymer formed may be distributed uniformly throughout the particle, or it may be present as a discrete phase. The discrete phase may exist as one or more polymeric domains, or as one or more shells. As used herein, "shell" refers to a discrete layer surrounding the bioactive compound. One or more shells may be formed around the biologically active compound.

A major advantage of the encapsulation techniques used in this invention is that the polymers are easily modified to provide varying properties to the particle. As a result, release of the bioactive compound from the particle may be controlled in a variety of ways and, therefore, delivery of the bioactive compound may be precise. In the case of pesticides, a number of problems are overcome using this invention. For example, the physical or toxicological properties of a pesticide may make certain uses unattractive. If a pesticide is volatile, high application rates may be required to maintain an effective dose. However, as exemplified below, encapsulation can reduce volatility losses substantially without reducing the effectiveness of the pesticide. For bioactive compounds which are dermally toxic, encapsulation can reduce the risk of using such material by preventing dermal absorption because when encapsulated, the toxic material can no longer come into direct contact with skin.

Alternately, varying the polymer properties can provide particles in which the site of application can be controlled. Decreasing the glass transition temperature ($T_g$) of the polymer will result in an encapsulated bioactive compound in which the polymer is soft and sticky. This is accomplished by increasing the relative proportion in the polymer of monomer units such as vinyl alcohol, vinyl acetate, butyl acrylate, longer chain acrylates, and the like. Preferably, to obtain a soft, sticky polymer, the $T_g$ of the polymer should be below the ambient temperature where the application of the bioactive material will occur. Most preferably, such polymers should have a $T_g$ less than 50 degrees Celcius. A greater difference between the $T_g$ and the ambient temperature will result in a softer, stickier particle. Sticky particles are especially advantageous when, for example, a pesticide is applied to a leaf surface. Such particles will cling to the leaf and resist wash-off by rain. Alternately, by making the polymer hard, through the use of higher $T_g$ monomers such as, for example, methacrylic acid, methyl methacrylate, styrene, and the like, the particle will not be sticky. That results in a particle which will be less likely to cling to a leaf surface. This situation is ideal when it is desirable to have the majority of bioactive material reach the soil.

In addition to varying the softness of the particle, one skilled in the art will understand that functional groups attached to the polymer may be used to vary the release of bioactive material. For example, by incorporating monomers containing acid functionality, such as, for example, methacrylic acid, a polymer is obtained which will release the bioactive material when exposed to an alkaline environment. One example of this use is in the application of a pesticide to be applied to alkaline soil. Using a high $T_g$ polymer with acid functionality will allow the particles to be applied to foliage. Because the polymer is not sticky, it is easily washed off the foliage onto the soil. Because soil is alkaline, the pesticide is released. In a similar manner, an insecticide may be encapsulated in a soft, sticky polymer with acid functionality. In this case the particle will cling to foliage. When subsequently consumed by a caterpillar, which has an alkaline gut, the insecticide is released.

Examples of pesticides which can be used in the compositions of the present invention include one or more of: (1) fungicides such as, for example, (a) nitrophenol derivatives such as dinocap, binapacryl, and 2-sec-butyl-4,6-dinitrophenyl isopropyl carbonate; (b) heterocyclic structures such as captan folpet, glyodine, dithianon, thioquinox, benomyl, thiabendazole, vinolozolin, iprodione, procymidone, triadimenol, triadimefon, bitertanol, fluoroimide, triarimol, cycloheximide, ethirimol, dodemorph, dimethomorph, thifuzamide, and, quinomethionate; (c) miscellaneous halogenated fungicides such as: chloranil, dichlone, chloroneb, tricamba, dichloran, and polychloronitrobenzenes; (d) fungicidal antibiotics such as: griseofulvin, kasugamycin and streptomycin; (e) miscellaneous fungicides such as: diphenyl sulfone, dodine, ethylene bis-isothiocyanate sulfide, methoxyl, 1-thiocyano-2,4-dinitrobenzene, 1-phenylthiosemicarbazide, thiophanate-methyl, and cymoxanil; as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy)pyrimidin-4-yloxy)phenyl)-3-methoxyacrylate; benzo(1,2,3)thiadiazole-7-carbothioic acid S-methyl ester: propamocarb; imazalil; carbendazim; myclobutanil; fenbuconazole; tridemorph; pyrazophos; fenarimol; fenpiclonil; and pyrimethanil; (2) herbicides, such as, (a) carboxylic acid derivatives, including benzoic acids and their salts; phenoxy and phenyl substituted carboxylic acids and their salts; and trichloroacetic acid and its salts; (b) carbamic acid derivatives, including ethyl N,N-di (n-propyl)thiolcarbamate and pronamide; (c) substituted ureas, (d) substituted triazines, (e) diphenyl ether derivatives such as oxyfluorfen and fluoroglycofen, (f) anilides such as propanil, (g) oxyphenoxy herbicides, (h) uracils, (i) nitriles, and (j) other organic herbicides such as dithiopy and, thiazopyr; and (3) insecticides, including acephate, aldicarb, alpha-cypermethrin, azinphos-methyl, bifenthrin, binapacryl, buprofezin, carbaryl, carbofuran, cartap, chlorpyrifos, chlorpyrifos methyl, clofentezine, cyfluthrin, cyhexatin, cypermethrin, cyphenothrin, deltamethrin, demeton, demeton-S-methyl, demeton-O-methyl, demeton-S, demeton-S-methyl sulfoxid, demephion-O, demephion-S, dialifor, diazinon, dicofol, dicrotophos, diflubenzuron, dimethoate, dinocap, endosulfan, endothion, esfenvalerate, ethiofencarb, ethion, ethoate-methyl, ethoprop, etrimfos, fenamiphos, fenazaflor, fenbutatin-oxide, fenitrothion, fenoxycarb, fensulfothion, fenthion, fenvalerate, flucycloxuron, flufenoxuron, fluvalinate, fonofos, fosmethilan, furathiocarb, hexythiazox, isazophos, isofenphos, isoxathion, methamidophos, methidathion, methiocarb, methomyl, methoxyfenozide, methyl parathion, mevinphos, mexacarbate, monocrotophos, nicotine, omethoate, oxamyl, parathion, permethrin, phorate, phosalone, phosmet, phosphamidon, pirimicarb, pirimiphos-ethyl, profenofos, promecarb, propargite, pyridaben, resmethrin, rotenone, tebufenozide, temephos, TEPP, terbufos, thiodicarb, tolclofos-methyl, triazamate, triazophos, andvamidothion.

Examples of pharmaceutical agents which can be used in the compositions of the present invention include one or more of: AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflamatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung suifactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media.

This invention also contemplates mixtures of more than one type of particle. Thus, one can use mixtures of particles with different bioactive materials, particles with mixtures of two or more different bioactive materials, different polymer compositions, different bioactive material to polymer ratios, and different sizes to obtain a wide variety of biological effects. These effects result from the different release rates or targets for the different particles. Such mixtures can be the result of mixing separately prepared particles or by preparing different particles at the same time through the use of seed emulsions of different properties. By appropriately varying the properties of the particle, particularly the polymer, one can obtain wide variations in the release characteristics of the bioactive compound. In some cases the release will be slow and consistent over time, in others it will be quick, either shortly after delivery or a predetermined time after delivery.

Conventional polymer encapsulation preparative methods result in broad distributions for the shapes and sizes of the particles. The preparative method disclosed in U.S. patent application Ser. No. 08/704,316 provides particles with a very narrow particle size distribution. In contrast, particles made by conventional techniques have particle size distributions greater than or equal to 1.5. Thus, the method disclosed in Ser. No. 08/704,316 is the preferred method for producing the polymer encapsulated bioactive compounds of this invention.

The uniform particles of this invention may be present as droplets dispersed in an aqueous phase which are then converted to polymer encased particles in which the biologically active compound forms a core surrounded by one or more polymeric shells. The particles so formed can then be dried to form a powder comprising individual particles surrounded by one or more polymer shells. Alternatively, the particles so formed may be used to produce a suspension concentrate To prepare the particles of the present invention using the method disclosed in Ser. No. 08/704,316, an aqueous emulsion of bioactive material is combined with an aqueous emulsion of seed particles. Alternatively, another liquid material may be used in place of, or in combination with, the bioactive material. The liquid material may be organic, inorganic or mixtures thereof. In addition, the liquid material may contain dissolved, or partially dissolved solid material. Organic shall mean to be comprised substantially of hydrogen and carbon atoms. Organic may also incorporate other atoms such as oxygen, sulfur, nitrogen and halogens and isotopes thereof. Inorganic shall mean to be comprised substantially of all other atoms not described herein as organic. Inorganic materials may also be derived from precursor materials that in and of themselves may or may not be inorganic. Preferably, the combined emulsions are mechanically agitated at a rate sufficient to cause intimate mixing of the two emulsions, but not so severe that shear forces cause coalescence or particle breakdown. The seed particles are swelled by the liquid material, forming droplets. The liquid material need not be a liquid at ambient temperatures, but it should be a liquid at the temperature at which swelling of the seed polymer is accomplished. Following this primary swelling, the droplets may optionally be further swelled by the addition of monomer and the monomer may then be polymerized.

In a preferred embodiment of the invention, the bioactive material, or a solution of the bioactive material is employed as the liquid. A mixture of two or more bioactive materials may be used.

The seed particles are prepared in an aqueous emulsion from one or more ethylenically unsaturated monomers. Emulsion polymerization techniques are known to those skilled in the art. For example, emulsion polymerization techniques are discussed in U.S. Pat. Nos. 3,037,952 and 2,790,736. Emulsion polymerization techniques are also discussed in *Emulsion Polymerisation Theory and Practice,* D. C. Blackley, Applied Science Publishers Ltd., London (1975). In emulsion polymerization methods, a surfactant is typically used, and the size of the seed formed is partly determined by the amount and type of surfactant. For purposes of the present invention, it is desirable to form seed with particle diameters of a size range from about 50 nanometers to about 1 micron, preferably from about 150 nanometers to about 500 nanometers, and more preferably about 200 nanometers (Wu et al., U.S. Pat. No. 5,237,004; see, for example, examples 1, 5, and 6). The particle size desired for the seed particles is determined by the target particle size for the biologically active compound containing particles. Larger seed diameters, up to about 5 microns, can be achieved by non-emulsion processes whereby an emulsion-derived seed is swollen with monomer and polymerized. Particles of a useful size range may be prepared with surfactant concentrations of from about 0.1 weight percent to about 5 weight percent, based on the total weight of monomers and biologically active compound, depending on the type of surfactant used. When non-ionic surfactants are used, it may be preferred to use up to about 10 weight percent surfactant. Examples of useful surfactants for the present invention include ionic surfactants such as, for example, sodium lauryl sulfate, sodium dioctylsulfosuccinate, sodium polyoxyethylene lauryl ether sulfate, sodium dodecyl benzenesulfonate; and non-ionic surfactants such as, for example, glycerol aliphatic esters, polyoxyethylene aliphatic esters, polyoxyethylene alcohol ethers; and stearic acid monoglyceride.

Throughout this application, the following abbreviations may be used:

MMA Methyl methacrylate
MAA Methacrylic acid
EA Ethyl acrylate
HEMA Hydroxyethyl methacrylate
Sty Styrene
NaDDBS Sodium dodecylbenzene sulfonate
DOSS Dioctyl sodium sulfosuccinate (also known as di-2-ethylhexyl sodium sulfosuccinate)
t-BPO tert-Butyl peroctoate
EtOAc Ethyl acetate
EtOH Ethyl alcohol
MDC Methylene chloride ($CH_2Cl_2$)
SEM Scanning electron microscope or scanning electron microscopy
PVOH Poly(vinyl alcohol)
DI deionized The seed particles comprise polymer chains. The seed particles may be formed by polymerization in the presence of a pre-seed emulsion. The pre-seed emulsion is an emulsion of polymeric particles and is also formed by well-known aqueous emulsion methods. The pre-seed polymer may be crosslinked. As is well known to those skilled in the art, crosslinking may be achieved by the use of polyethylenically unsaturated monomers such as polyethylenically unsaturated acrylates and methacrylates or polyethylenically unsaturated aromatic monomer such as divinyl benzene. Examples of polyethylenically unsaturated monomers useful as crosslinkers for forming the pre-seed emulsion include allyl methacrylate (ALMA); dicyclopentenyl acrylate and methacrylate; glycidyl methacrylate; glycidyl acrylate; acrylate and methacrylate esters of neopentyl glycol monodicyclopentenyl ether, epoxy-containing acrylates and methacrylates; divinyl benzene and dicyclopentenyloxyethyl acrylate and methacrylate.

Ethylenically unsaturated monomers useful in forming the seed and pre-seed particles include vinylaromatic monomers such as styrene, α-methylstyrene, vinyltoluene, vinylanthracene; ethylvinylbenzene and vinylnaphthalene. Non-aromatic vinyl monomers, such as vinyl acetate, hydrolyzed vinyl acetate, vinyl chloride, acrylonitrile, (meth)acrylic acids and alkyl esters or amides of (meth)acrylic acids (such as methyl acrylate, methyl methacrylate, ethyl acrylate, butyl methacrylate, methyl methacrylamide and dimethylaminopropyl methacrylamide), may also be used in forming the seed particles of the present invention, in addition carboxylic-acid-containing low molecular weight polymers, those with molecular weights of less than about 10,000, are included within the scope of the present invention. The expression (meth)acrylic acid is intended to include methacrylic acid and acrylic acid; the expression is used similarly in, e.g., methyl (meth)acrylate, ethyl (meth)acrylate, and the like. Also useful are halogenated aromatic monomers, such as, for example, pentafluorophenyl methacrylate; and halogenated non-aromatic monomers, such as, for example, haloalky acrylates and methacrylates. Also useful for forming seed and pre-seed particles are monomers containing crosslinkable functional groups when subjected to the proper conditions such as UV irradiation. Such materials include hydroxy-methacryloxy-propyl 2-benzoylbenzoate. Copolymers, such as those prepared from mixtures any of the aforementioned monomers, may also be prepared in forming the seed and pre-seed particles of the present invention.

Chain transfer agents such as, for example, mercaptans, polymercaptans, and polyhalogen compounds may optionally be added to the monomers in order to moderate molecular weight. Specific examples include alkyl mercaptans such as t-dodecyl mercaptans and hexanethiol; alcohols such as isopropanol, isobutanol, lauryl alcohol, and t-octyl alcohol; and halogenated compounds such as carbon tetrachloride, tetrachloroethylene, and trichlorobromoethane. For forming the seed particles, the amount of chain transfer agent required may be from about 5 percent to about 20 percent, although amounts above 20 percent may be required depending on the molecular weight desired. Typically the polymer chains have a molecular weight from below about 200,000, preferably below about 100,000, and most preferred from about 200 to about 10,000. The lower molecular weights are preferred due to their inherent ability to swell.

The amount of seed in the seed emulsion is determined by the final desired concentration of seed in the mixture, and the desired final size of the liquid domains. The emulsion of seed particles may range up to about 50 percent seed particles by weight, and has no theoretical lower limit.

For forming droplets containing the bioactive material, an emulsion of the compound is used. The emulsion of the bioactive material may be from 1 percent to 95 percent biooactive material by weight, preferably from 10 percent to 70 percent, most preferably 20 to 50 percent. The emulsion of bioactive material is combined with the aqueous emulsion of seed particles. The order of addition is not critical.

In order to ensure that the bioactive material will be incorporated into the seed, optionally a transport agent be used. The transport agent is also referred to as a co-solvent, and may be one or more materials selected from solvents and monomers. The co-solvent may also be a mixture comprising one or more solvents and one or more monomers. A suitable co-solvent is preferably immiscible or slightly miscible with water, for example less than 20 percent soluble in water, and should act as a solvent for the biologically active compound. A mixture of co-solvents may be used.

Examples of solvents useful as transport materials in the method of the present invention are: $C_1$–$C_{12}$ alkyl esters such as ethyl acetate; halogenated $C_1$–$C_{12}$ alkanes such as methylene chloride; $C_1$–$C_{12}$ alkyl ethers such as ethyl ether; cyclic alkyl ethers such as 2,5-dimethyltetrahydrofuran and 2,2,5,5-tetramethyltetrahydrofuran; $C_1$–$C_{12}$ ketones such as 2-hexanone; $C_1$–$C_{12}$ alcohols such as 1-pentanol, and alkylbenzenes such as mixed xylenes. Ethyl acetate is the preferred solvent if it is to be removed by evaporation prior to polymerization. Otherwise, it is preferable to use the monomer or a high boiling solvent such as, for example, mixed alkylbenzenes.. Examples of monomers useful as transport materials in the method of the present invention are: $C_1$–$C_{20}$ acrylates and methacrylates; halogenated $C_1$–$C_{20}$ acrylates and methacrylates; aryl acrylates and methacrylates; halogenated aryl acrylates and methacrylates; hydroxy ethyl acrylate and methacrylate; hydroxypropyl methacrylate; hydroxypropyl acrylate; styrene, vinyl ethers; vinyl halides; and vinylidene halides. If a monomer is used, the monomer composition will be determined by the desired composition of the optional polymeric shell, discussed herein below. The preferred monomer will be determined by the transport properties of the bioactive material.

Alternatively, the transport material may be a macromolecular organic compound having a hydrophobic cavity. A "macromolecular organic compound having a hydrophobic cavity" is a polymeric molecule, typically cylindrical or approximately cylindrical, which typically has a hydrophilic exterior but has a hydrophobic interior. These compounds may be used to transport hydrophobic substances in an aqueous environment. Such compound, useful in method of the present invention, include cyclodextrin and derivatives thereof; cyclic oligosaccharides having a hydrophobic cavity, such as cycloinulohexose, cycloinuloheptose, and cycloinuloctose; calyxarenes; and cavitands; cyclodextrin is a preferred compound. The selection of cyclodextrin and derivatives thereof useful in the present invention is determined by the solubility of the cyclodextrin and cyclodextrin derivatives in the aqueous medium and by the solubility of the species formed by the association of the transport agent and the biologically active compound. Suitable cyclodextrins useful in the method of the present invention include: α-cyclodextrin, β-cyclodextrin, and γ-cyclodextrin. The preferred cyclodextrin derivative is methyl-substituted β-cyclodextrin.

The amount of optional transport agent to be used is partly determined by the composition of the transport agent. If the transport agent is a cyclodextrin, the weight ratio of cyclodextrin to bioactive compound may range from about 1:1000 to about 10:100 and is typically from about 1:100 to about 5:100, more typically about 2:100. The lower limit is determined by such things as the desired rate of transport. The upper limit is determined by the required stability of the aqueous system. If the transport agent is a solvent or monomer, the ratio of transport agent to bioactive material is less critical, and will depend upon the desired particle morphology. A monomer may be used as the transport agent. The amount of monomer used will be determined by the desired thickness of the shell, and by whether additional monomer will be used in forming the shell.

In addition to the bioactive material and the transport agent, there may also be present in the aqueous medium one or more monomers. The monomers may already be present if they have been used as a transport agent. Alternatively, one or more monomers may be added, for example, in the form of an aqueous emulsion. Monomers useful in this step include the ethylenically unsaturated monomers listed above. The total amount of monomer used may range from 5 weight percent to 95 weight percent, preferably 10 percent to 50 percent, and most preferably 15 to 35 percent based on the total weight of monomer and bioactive material. The total amount of monomer within this range includes monomer used in forming the seed, monomer optionally used as a cosolvent, and monomer used in subsequent polymerizations discussed hereinbelow. The amount of monomer may be adjusted depending upon the efficiency of polymerization of the monomers, also called the conversion.

The one or more monomers may be polymerized in the presence of the bioactive material and the transport agent. The monomers may be polymerized by aqueous suspension, emulsion, or dispersion polymerization. These methods are known in the art. Polymerization may be carried out as a batch, semi-batch, continuous, or semi-continuous reaction. Preferably, the polymerization is carried out as a semi-batch reaction. The present invention is not limited to free-radical polymerization. Other forms of polymerization may also be used such as, for example, polycondensation (see U.S. Pat. No. 3,577,515).

Examples of monomers useful in the polymerization include styrene, α-methylstyrene, vinyltoluene, ethylvinylbenzene and vinylnaphthalene, vinyl anthracene, vinyl acetate, hydrolyzed vinyl acetate, vinyl halides, vinylidene halides, acryloyl and methacryloyl functional silanes and siloxanes, vinyl silanes and siloxanes, halogenated aromatic monomers, acrylonitrile, acrylic acid, methacrylic acid, $C_1$–$C_{20}$ alkyl esters of acrylic acid, halogenated $C_1$–$C_{20}$ alkyl esters of acrylic acid, $C_1$–$C_{20}$ alkyl esters of methacrylic acid, halogenated $C_1$–$C_{20}$ alkyl esters of methacrylic acid, $C_1$–$C_{20}$ alkyl amides of acrylic acid, $C_1$–$C_{20}$ haloalkyl amides of acrylic acid and methacrylic acid, $C_1$–$C_{20}$ alkyl amides of methacrylic acid, and maleic acid and its esters, half esters, amides, half amides, and anhydride. Suitable polycondensation monomers are provided in U.S. Pat. No. 3,577,515, see columns 7 and 8. Halogenated aromatic monomers include aromatic rings having halogen substituents directly attached to the ring, or present on alkyl groups attached to the ring, such as for example a trifluoromethyl group. Examples of halogenated aromatic monomers include pentaflurophenyl acrylate and pentafluorophenyl methacrylate.

The polymerization of the one or more monomers may be used to form a polymeric shell around the bioactive material. Polymer shells may be formed around the bioactive material using monomers that may contain one or more functional groups which may be converted to an ionic moiety. Alternatively, polymer shells may be formed around the bioactive material using monomers that do not contain ionic moieties.

Monomers containing functional groups which may be converted to an ionic moiety include hydrolyzable esters and anhydrides, monomers containing carboxylic acid moieties and monomers containing amine moieties. Examples of monomers containing carboxylic acid moieties include acrylic acid, methacrylic acid, (meth)acryloxypropionic acid, itaconic acid, citraconic acid, crotonic acid, maleic acid, maleic anhydride, fumaric acid, monomethyl maleate, monomethyl fumarate, monomethyl itaconic acid, and mixtures of methacrylic and acrylic acid. The use of polymerizable carboxylic acid containing low molecular weight oligomers, those with molecular weights of less than about 10,000 molecular weight, are included within the scope of the present invention. Examples of monomers containing amine moieties include 2-aminoethyl methacrylate, N-methacryloxypiperidine, dimethylaminoethyl methacrylate, vinyl pyridine, 2-(dimethylamino)ethyl (meth)acrylate, 2-(tert-butylamino)ethyl (meth)acrylate, 3-(dimethylamino)propyl (meth)acrylamide, 2-(diethylamino)ethyl (meth)acrylate and 2-(dimethylamino)ethyl (meth)acrylamide. Preferred are monomers having acidic moieties and having a pKa of 3 or higher, such as methacrylic acid and mixtures of methacrylic acid and acrylic acid. Most preferred is methacrylic acid.

Relative to the total monomers present, the amount of monomer conversion to ionic moieties constitutes from zero up to about 70 percent by weight of the total monomers, preferably up to 40 percent, more preferably 15 percent to 35 percent. However, the amount of monomer containing convertible functional groups is not limited to 50 percent, because the amount of conversion may be less than 100 percent of the available convertible functional groups.

Other monomers, not having functional groups convertible to an ionic moiety but which are useful in forming the polymeric shell according to the method of the present invention, and may be present in the aqueous medium, include hydroxy and di-hydroxy alkyl acrylates and methacrylates, such as for example hydroxyethyl acrylate, hydroxyethyl methacrylate, hydroxypropyl methacrylate, and hydroxypropyl acrylate. When used, the amount is preferably 1 percent to 30 percent, and most preferably 10 percent to 20 percent by weight, based on the total weight of all monomers.

The solubility of the bioactive material in the polymer to be formed may influence the need for the use of a monomer with functional groups convertible to an ionic moiety in order to form a discrete shell of uniform thickness.

Also useful are monomers which have functional groups which provide stabilization against ultraviolet (UV) radiation. Such monomers are particularly advantageous when the bioactive material is unstable to UV radiation. Examples of such monomers includes polymerizable hindered amines. Another type of UV stabilizing monomer is 4-methacryloxy-2-hydroxybenzophenone.

The functional groups may be converted to ionic moieties, for example, by acid-base reaction, or hydrolysis of said functional groups. For example, to carry out an acid base reaction, a base may be added when acid functional monomers are used, and an acid may be added when basic functional monomers have been used. The amount of acid or base is dependent upon the functional group and upon the degree of ionization desired. Bases useful include amines such as ammonia, and organic amines such as methyl amine, triethylamine, piperidine, pyridine, mono, di-, and tri- alkyl amines, aryl amines, aniline, aminonaphthalene, other aryl amines; and hydroxides such as sodium hydroxide. Acids useful include $C_1$–$C_{12}$ aliphatic and aromatic monocarboxylic acids, dicarboxylic acids, and corresponding anhydrides and mixtures thereof. Specific examples include benzoic acid, m-toluic acid, p-chlorobenzoic acid, o-acetoxybenzoic acid, azelaic acid, sebacic acid, octanoic acid, cyclohexanecarboxylic acid, lauric acid, and monobutyl phthalate. Inorganic acids such as hydrochloric acid, sulfuric acid, and phosphoric acid may also be used. Also useful are sulfonic acids such as para-toluene sulfonic acid and methane sulfonic acid, and phosphonic acids.

For example, typically to achieve substantially complete ionization when a monomer containing a monocarboxylic acid function is used, ammonia may be added. The amount of ammonia added is at least one molar equivalent based on monocarboxylic acid functional monomer, and preferably about 1.5 molar equivalents. Typically, to achieve complete ionization when a monomer containing an amine functional group is used, acetic acid may be added. The amount of acetic acid added is at least one molar equivalent, and preferably about 1.5 molar equivalents.

The optional conversion of the functional groups to ionic moieties is carried out as a final step in the process for forming the shell. The entire process for making the particles may be summarized as follows. A solution of biologically active compound, initiator, and monomer is emulsified and added to an emulsion of the seed. After the seed is swelled by the biologically active compound, monomer and initiator, and has formed uniformly sized droplets, then the mixture may be heated to the polymerization temperature for the monomer/initiator combination. Alternatively, heating and swelling may be carried out simultaneously. When polymerization is complete, the acid or base is added.

The polymeric shell may be crosslinked subsequent to the polymerization to form the shell polymer, preferably subsequent to the conversion of functional groups to ionic moieties. Crosslinking may be accomplished by the reaction of residual double bonds or functional groups, with or without the addition of a catalyst or other crosslinking agents. Crosslinking agents described above for use in crosslinking the pre-seed polymer are also useful in crosslinking the polymeric shell. In particular, if monomers such as acetyl acetoxy ethyl methacrylate were used in forming the polymeric shell, the subsequent reaction with formaldehyde or other aldehydes can serve to crosslink the polymeric shell. Other methods of crosslinking include the addition of difunctional molecules which can serve as crosslinking agents such as for example aziridine, carbodiimide, and diisocyanates. Also useful are metal salt methods of crosslinking known to those skilled in the art. Of further utility are monomers containing moieties useful as photoinitiators. Polymer chains containing these moieties can be subjected to photocuring methods known in the art to achieve free radical crosslinking.

For example, if an epoxy-containing monomer was used in forming the shell polymer, a base may be utilized to effect crosslinking. The base may be present as a result of the shell formation, or may be added. The amount of base present, either in free or complexed form after shell formation, will generally be sufficient to effect crosslinking. However, additional base may be added to achieve a greater degree of crosslinking. Typically, a full molar equivalent is not required. The amount of base required may be referred to as a "catalytic amount", meaning that only an amount of base required to facilitate the reaction is needed since the base is not consumed in the reaction.

Crosslinking by means of residual double bonds may require inducing a reaction by, for example, UV irradiation, optionally in the presence of a photosensitizing agent, or addition of free-radical initiator. Other crosslinking agents relying on free-radical reactions, which may be, for example, thermally initiated, include polyfunctional acrylates and methacrylates. Specific examples are allyl methacrylate and 1,1,1-trimethylolpropane tri(meth)acrylate. When one of the monomers is itself a photoinitiator, free radicals can be created on previously inert polymer chains, leading to reaction with other similarly activated chains to give crosslinking.

Formation of more than one shell may be accomplished by sequential polymerization in more than one stage. It is preferred that the hydrophilicity of the polymers in each stage not be the same after neutralization. Hydrophilicity refers to the affinity of the polymers for the aqueous phase. Polymers of sufficiently different hydrophilicity will form, upon neutralization, discrete adjacent shells or interpenetrating shells representing a gradient of composition. The neutralization of the polymer stages is a preferred embodiment and is not required. The difference in hydrophilicity may be accomplished by using different monomers in each stage, or by using the same monomers but in different ratios. Formation of more than one shell may also be accomplished by simultaneous polymerization of monomers having reactivities sufficiently different that they would not be likely to react together to form a random copolymer.

Optionally, additional monomer, or mixtures thereof, may be added and polymerized following the formation of the one or more shells. The additional monomer is polymerized on or in the particle including the one or more shells. This forms another external polymeric shell, useful for controlling such properties as: the structural integrity and flexibility of the particle; anchoring forces at the interface between the bioactive material and polymer wall; film formation and adhesion, adhesion to leaf surfaces, and compatibility with vascular systems and tissues in both plants and animals. Initiator may be added prior to, concurrently with, or subsequent to, the addition of the additional monomer. It is preferred that the composition of the additional monomers be chosen so that the additional monomers, when polymerized, form a layer adjacent to the existing shell(s) and bounded on its other surface by water.

The polymeric shell may optionally be functionalized following formation. For example, if functional groups exist on the interior surface of the innermost shell or the exterior surface of the outermost shell, derivatives may be formed at the desired surface. Examples of reactions by which functionalization may be accomplished include esterification, salt formation, complexation, polymerization, and substitution reactions. Such reactions may be carried out utilizing methods known to those skilled in the art. Functionalization of polymers is discussed, for example, in U.S. Pat. No. 4,283,499.

An optional additional step in the method of the present invention is the removal of the transport agent. The manner in which removal is carried out depends upon the composition of the transport agent. If a macromolecular organic compound having a hydrophobic cavity, such as for example a beta cyclodextrin or methylated beta cydodextrin, has been used as the transport agent, it may be removed from the particle by adding a decomplexing agent. A decomplexing agent is a material having an affinity for the macromolecular compound having a hydrophobic cavity. The decomplexing agent may be added before polymerization or after polymerization of any monomers present. If a monomer has been polymerized by emulsion polymerization in the presence of the macromolecular compound and the biologically active compound, decomplexing may occur automatically before the polymer is formed and further decomplexing is generally not necessary. Once decomplexation has been carried out, the macromolecular organic compound may still remain in the aqueous phase. Optionally, it may be removed from the aqueous phase by, for example, diafiltration. The particles may also be separated from the aqueous phase by centrifugation or settling, followed by decantation. Suitable decomplexing agents include conventional surface active agents, such as, for example, nonionic, anionic and cationic surfactants. Other suitable decomplexing agents include organic solvents such as, for example, ethanol. The amount of decomplexing agent used is preferably 1 to 10 moles of decomplexing agent per mole of macromolecular organic compound having a hydrophobic cavity, to achieve complete decomplexation.

If an organic compound, including monomers and solvents, is used as the transport agent, it may also be removed. The organic compound is preferably, but not necessarily removed before polymerization. The organic compound may be removed by evaporation. If a component of the liquid domain contained within the particle further comprises a solid dissolved in a liquid, the liquid may be removed by evaporative or other means from the particle, leaving a solid surrounded by the polymer shell with or without additional void space.

The particles may be isolated in powder form after removal of the aqueous phase. Isolated particles may be redispersed in aqueous or nonaqueous liquids forming suspension concentrates. Following isolation, it may be desired, for example, to form a mixture of particles having two or more sizes. This is particularly advantageous if two or more incompatible bioactive materials are to be delivered, or applied, at the same time. A mixture may be formed by combining isolated particles or, preferably, by combining dispersions of particles. Alternatively, a mixture of particle sizes may be obtained by carrying out the primary swelling described hereinabove, using seed particles having different particle sizes. It is also possible to form a mixture of particles of selected sizes by using the method to produce separate batches of particles having desired particle sizes, and combining the differently sized particles together in the desired proportions. This provides a mixture of discrete particle sizes, and allows for the exclusion of particular sizes. Particles of the same or different sizes, and having different seed or shell compositions, or swelled with different materials, may be combined.

EXAMPLES

Reducing the volatilization of an herbicidal bioactive material

Example 1

Encapsulation of dithiopyr with poly (acrylate/styrene)
1. Turn on shaker bath and set for 85° C.
2. Dissolve 18.753 gm dithiopyr (S,S'-dimethyl 2-difluoromethyl-4-(2-methylpropyl)-6-trifluoromethyl-3,5-pyridinedicarbothioate) in 6.28 gm of diisodecylphthalate and 50.00 gm of ethyl acetate in a 250 mL reactor jar.
3. Add 31.75 gm deionized water, 12.403 gm of 2% DOSS solution in water and, 2.97 gm of 50.8% methyl B cyclodextrin solution to the organic mixture prepared in Step #2.
4. Homogenize the mixture prepared in Step #3 at 10 to 12 thousand RPM in an Omni International Model GLH homogenizer for 90 sec, let it rest 60 sec, and homogenize for another 90 sec.
5. Add 13.45 gm of a 29.2% seed emulsion (a polymer emulsion latex 29.2% polymer by weight, 0.562 micron particle size, poly(butyl acrylate/styrene/hexanethiol//82/18/19)) and 25.80 gm of deionized water to the homogenized emulsion prepared in Step #4. Invert reactor jar ten times to mix. Place 250 mL reactor jar in shaker bath at 85° C. for 120 min of swelling.
6. Place swollen seed particles into 75° C. bath, sparge swollen sample with nitrogen until 55.73 gm of volatiles are removed, and swollen seeds are free of ethyl acetate.
7. Add 17.0 gm monomer mix (2.5% MAA/20% HEMA/45.15% MMA/32.35% STY), 0.595 gm of tert-butyl peroctoate (tBPO), 2.805 gm of 2% DOSS solution to 13.6 gm of deionized water in a 2 oz vial. Homogenize monomer mix. Warm monomer emulsion to 50° C.
8. Heat 70.23 gm dilution deionized water to 50° C.
9. Cool swollen seed particles from Step #6 to about 50° C., add 25.13 gm warm monomer emulsion from Step #7 and 70.23 gm warm water from Step #8 to make a polymer preform.
10. Place the polymer preform from Step #9 into 85° C. shaker bath for 1 hour and then raise bath temperature to 95° C. and hold for another hour.
11. Filter and cool product dispersion.

The resulting encapsulated bioactive compound has a relatively hard shell and very monodisperse particles with a size of about 1 micron (by scanning electron microscopy, SEM).

Example 2

Encapsulation of dithiopyr with poly (acrylate/styrene)
1. Turn on shaker bath and set for 85° C.
2. Add 18.753 gm dithiopyr to 6.256 gm of alkylbenzene based solvent (Aromatic™200 solvent, Exxon Corp.) in a 250 mL reactor jar. Heat to 55° C. to dissolve mixture.
3. Add 81.95 gm deionized water, 12.48 gm of 2% DOSS solution and, 2.96 gm of 50.8% methyl B cyclodextrin solution to the organic mixture prepared in Step #2. Heat all components to 55° C. before homogenization.
4. Homogenize the warmed mixture prepared in Step #3 at 10 to 12 thousand RPM for 90 sec, let it rest 60 sec and, homogenize for another 90 sec. Homogenize in a preheated 55° C. water bath.
5. Add 39.48 gm of a 29.2% of a seed emulsion (a polymer emulsion latex 29.2% polymer by weight, 0.562 micron particle size, poly(butyl acrylate/styrene/hexanethiol//82/18/19)) prewarmed to about 55° C. to the homogenized emulsion prepared in Step #4. Invert reactor jar ten times to mix. Place 250 mL reactor jar in shaker bath at 85° C. for 124 min of swelling.

6. Place swollen seed particles into 55° C. bath, sparge swollen sample with nitrogen until swollen seed dispersion is at 55° C.
7. Add 17.07 gm monomer mix (2.5% MAA/20% HEMA/45.15% MMA/32.35% STY), 0.596 gm of tert-butyl peroctoate (tBPO), 2.818 gm of 2% DOSS solution to 13.615 gm of deionized water in a 2 oz vial. Homogenize monomer mix. Warm monomer emulsion to 50° C.
8. Heat 19.15 gm dilution deionized water to 55° C.
9. When swollen seed particles from Step #6 are at 55° C., add 33.192 gm warm monomer emulsion from Step #7 and 19.15 gm warm water from Step #8 to make a polymer preform.
10. Place the polymer preform from Step #9 into 85° C. shaker bath for 1 hour and then raise bath temperature to 95° C. and hold for another hour.
11. Filter and cool product dispersion.

The resulting particle has a relatively soft shell due to the alkylbenzenes solvent which softens the polymer. The particle size is about 0.5 micron and relatively monodisperse by SEM.

Example 3
Encapsulation of dithiopyr with poly (acrylate/styrene)
1. Turn on shaker bath and set for 85° C.
2. Add 18.81 gm dithiopyr to 6.26 gm of alkylbenzene based solvent (Aromatic 200™, Exxon Corp.) in a 250 mL reactor jar. Heat to 55° C. to dissolve mixture.
3. Add 81.933 gm deionized water, 12.463 gm of 2% DOSS solution (DOSS, 75% in ethanol) and, 2.946 gm of 50.8% methyl B cyclodextrin solution to the organic mixture prepared in Step #2. Heat all components to 55° C. before homogenization.
4. Homogenize the warmed mixture prepared in Step #3 at 10 to 12 thousand RPM for 90 sec, let it rest 60 sec and, homogenize for another 90 sec. Homogenize in a preheated 55° C. water bath.
5. Add 39.477 gm of a 10.0% of a seed emulsion (a polymer emulsion latex 10.00% polymer by weight, 0.562 micron particle size, poly(butyl acrylate/styrene/hexanethiol//82/18/19)) prewarmed to about 55° C. to the homogenized emulsion prepared in Step #4. Invert reactor jar ten times to mix. Place 250 mL reactor jar in shaker bath at 85° C. for 120 min of swelling.
6. Place swollen seed particles into 55° C. bath, sparge swollen sample with nitrogen until swollen seed dispersion is at 55° C.
7. Add 17.014 gm monomer mix (2.5% MAA/20% HEMA/45.15% MMA/32.35% STY), 0.598 gm of tert-butyl peroctoate (tBPO), 2.810 gm of 2% DOSS solution to 13.161 gm of deionized water in a 2 oz vial. Homogenize monomer mix. Warm monomer emulsion to 50° C.
8. Heat 17.143 gm dilution deionized water to 55° C.
9. When swollen seed particles from Step #6 are at 55° C., add 24.632 gm warm monomer emulsion from Step #7 and 17.143 gm warm water from Step #8 to make a polymer preform.
10. Place the polymer preform from Step #9 into 85° C. shaker bath for 1 hour and then raise bath temperature to 95° C. and hold for another hour.
11. Filter and cool product dispersion.

The particles produced by this process are relatively soft shelled and relatively monodisperse with a particle size of about 1.0 micron by SEM.

Example 4
Encapsulation of dithiopyr with poly(acrylate/styrene)
1. Turn on shaker bath and set for 55° C.
2. Add 17.924 gm dithiopyr to 5.982 gm of alkylbenzene based solvent in a 250 mL reactor jar. Heat to 55° C. to dissolve mixture.
3. Pre-warm 13.20 gm monomer mix (2.5MAA/20HEMA/45.15MMA32.35STY), and 0.465 gm of tBPO to 55° C. and add to the organic mixture prepared in Step #2.
4. Pre-warm 8.001 gm deionized water, 6.609 gm of 2% DOSS solution and, 1.553 gm of a 52.5% methyl B cyclodextrin solution to 55° C. and add to the organic mixture prepared in Step #3. Heat all components to 55° C. before homogenization.
5. Homogenize the warmed mixture prepared in Step #4 at 10 to 12 thousand RPM in an Omni International Model GLH homogenizer for 90 sec, let it rest 60 sec and, homogenize for another 90 sec. Homogenize in a preheated 55° C. water bath.
6. Add 29.132 gm of a 10.0% seed emulsion (a polymer emulsion latex 10.00% polymer by weight, 0.562 micron particle size, poly(butyl acrylate/styrene/hexanethiol//82/18/19)) prewarmed to about 55° C. to the homogenized emulsion prepared in Step #5. Invert reactor jar ten times to mix. Place 250 mL reactor jar in shaker bath at 55° C. for 95 min of swelling.
7. Heat 117.212 gm dilution deionized water to 55° C.
8. Add 117.212 gm warm water from Step #7 to swollen seed particles of Step #6 to make polymer preform.
9. Place polymer preform from Step #8 into 70° C. shaker bath for 30 minutes and then raise bath temperature to 85° C. and hold for another hour. And then raise bath temperature to 95° C. and hold for another hour.
10. Filter and cool product dispersion.

This process is conducted as a "one-step" process. As a result, the particles were not as uniform in size by SEM. In addition, some dithiopyr was not encapsulated.

A portion of each Example was then applied to glass microscope slides and the amount of dithiopyr remaining on the slides was evaluated after holding for varying periods of time at 30° C. and 50% relative humidity. The results of these evaluations are in the following table.

Slide Volatility Results
% Dithiopyr Remaining on Glass Slide vs Hours After Spray

| Hours | Ex. 1 | Ex. 2 | Ex. 3 | Ex. 4 | 1EC | 25WP |
| --- | --- | --- | --- | --- | --- | --- |
| 0 | 100.00% | 100.00% | 100.00% | 100.00% | 100.00% | 100.00% |
| 3 | | | | | 78.46% | |
| 6 | | | | | 65.06% | 91.39% |
| 9 | | | | | 56.73% | |
| 12 | 101.12% | 70.81% | 86.02% | 89.53% | 37.07 | 76.05% |
| 24 | 96.97% | 57.09% | 85.51% | 87.32% | 17.17% | 46.97% |
| 48 | 91.39% | 44.34% | 75.01% | 76.12% | | 9.09% |

-continued

Slide Volatility Results
% Dithiopyr Remaining on Glass Slide vs Hours After Spray

| Hours | Ex. 1 | Ex. 2 | Ex. 3 | Ex. 4 | 1EC | 25WP |
|---|---|---|---|---|---|---|
| 72 | 89.75% | 39.67% | 72.37% | 72.89% | | 2.73% |
| 96 | 87.89% | 41.11% | 68.71% | 76.32% | | |

1EC—Commercial dithiopyr formulation, Dimension® 1E Herbicide Emulsifiable Concentrate, Rohm and Haas Co.
25WP—Dithiopyr 25% wettable powder formulation prepared by blending dithiopyr (27%, Rohm and Haas Co.), Hi-Sil® carrier(5%, PPG), Barden Clay (61%, J. M. Huber Corp.), Polyfon® H dispersant (5%, Westvaco Polychemicals), and Stepanol® ME surfactant (2%, Stepan Co.) (all percentages by weight) followed by hammer then air milling.

These data indicate that by encapsulating the bioactive material (dithiopyr) loss due to volatility is greatly reduced compared to two different non-encapsulated dithiopyr formulations.

To confirm that even though the volatility loss was reduced through encapsulation the bioactive material would still be effective, the efficacy of Examples 1–4 was compared with the 1EC formulation. In each test, the sample was suspended in water and applied directly to the soil at the application rate specified. For the "No Delay" examples, the crabgrass was seeded just after application. For the "7 Day Delay" examples, the crabgrass was seeded 7 days after application and then lightly covered with additional soil.

| Seeding[2] | Percent Crabgrass Control[1] 21 Days After Treatment | | | | |
|---|---|---|---|---|---|
| | Ex. 1 | Ex. 2 | Ex. 3 | Ex. 4 | 1EC |
| No Delay | 80 | 94 | 80 | 75 | 98 |
| 7 Day Delay | 63 | 58 | 51 | 70 | 66 |

[1]=Percent control averaged for application rates of 19, 38, 75, and 150 gm/Ha.
[2]=No Delay—Herbicide applied and crabgrass seeded on the same day, 7 Day Delay—Herbicide applied, treatment aged in greenhouse 7 days and then overseeded with crabgrass.

Comparison Example
Encapsulation of dithiopyr with polyurea
This process is similar to that disclosed in U.S. Pat. Nos. 4,280,833 and 4,417,916 (Monsanto Company).
1. Add 4.20 gm of poly(vinyl acetate/vinyl alcohol) (Airvol™ 205) to 252.0 gm of deionized water while stirring in a four ounce jar the night before homogenization in Step #7. This is the first step in preparing the aqueous emulsifier and stabilizer.
2. Add 45.3 gm dithiopyr technical to 10.26 gm of xylene and 2.40 gm of diisodecyl phthalate in a two ounce jar. Melt this mixture in a steam bath.
3. Hold organic mixture from Step #2 at about 60° C. until step #6.
4. Add 0.84 gm of DOSS in ethanol solution (Monawet™ MO-70E) to the solution prepared in Step #1 on the previous day. Heat this with stirring to 50° C.
5. Add 0.91 gm of ethylenediamine and 0.37 gm of triethylenetetraamine to 54.45 gm of deionized water in a two ounce jar. Cap and shake to mix. Transfer the mix to the addition funnel of the reactor.
6. Add 4.89 gm of oligomeric diphenylmethane diisocyanate (Mondur™ MRS) to the 60° C. organic mixture prepared in Step #3. Swirl to mix.
7. Combine the 50° C. solution of Step 4 and the 50° C. organic mixture of Step #6 in a 1.0 L 3 neck round bottom reactor in a heating mantel at 52 C., and homogenize at 13,500 rpm using a Janke & Kunkel IKA—Labortechnik Ultra-Turrax T25S1 homogenizer for 4 minutes.
8. Reduce homogenizer speed to 8,740 rpm and continue to homogenize for 3 minutes.
9. Add amine dropwise from an addition funnel with homogenizer running over 6.5 minutes, remove the homogenizer, and insert a flat blade turbine to maintain agitation.
10. Hold at 500° C. for about 11.5 min after amine addition, change set point to 35° C. and hold about 35 min, turn off heating mantle, lower heating mantle.
11. When reactor is cool enough to handle, pour dispersion into an eight ounce jar.

This example was evaluated in a manner similar to that of Examples 1–4. By SEM, the sample had a broad particle size distribution. It was found that the volatility was also reduced significantly, almost no measurable loss of dithiopyr. However, when evaluated for activity against crabgrass, the material was only 15 percent as active, on average, as a sample prepared in a manner similar to Examples 1–4.

Example 5
Encapsulation of thiazopyr with poly (acrylate/styrene)
1. Turn on shaker bath and set for 85° C.
2. Dissolve 18.82 gm thiazopyr in 6.32 gm of diisodecylphthalate and 50.00 gm of ethyl acetate in a 250 mL reactor jar.
3. Add 31.75 gm deionized water, 12.54 gm of 2% DOSS solution in water and, 2.998 gm of 50.8% methyl B cyclodextrin solution to the organic mixture prepared in Step #2.
4. Homogenize the mixture prepared in Step #3 at 10 to 12 thousand RPM in an Omni International Model GLH homogenizer for 90 sec, let it rest 60 sec, and homogenize for another 90 sec.
5. Add 13.47 gm of a 29.2% of a seed emulsion (a polymer emulsion latex 29.2% polymer by weight, 0.562 micron particle size, poly(butyl acrylate/styrene/hexanethiol//82/18/19)) and 25.816 gm of deionized water to the homogenized emulsion prepared in Step #4. Invert reactor test tube ten times to mix. Place 250 mL reactor jar in shaker bath at 85° C. for 120 min of swelling.
6. Place swollen seed particles into 75° C. bath, sparge swollen sample with nitrogen until 58.139 gm of volatiles are removed, and swollen seeds are free of ethyl acetate.
7. Add 17.0 gm monomer mix (2.5% MAA/20% HEMA/45.15% MMA/32.35% STY), 0.667 gm of tert-butyl peroctoate (tBPO), 2.85 gm of 2% DOSS solution to 13.7 gm of deionized water in a 2 oz vial. Homogenize monomer mix. Warm monomer emulsion to 65° C.
8. Heat 70.23 gm dilution deionized water to 50° C.
9. Cool swollen seed particles from Step #6 to about 65° C., add 24.82 gm warm monomer emulsion from Step #7 and 72.81 gm warm water from Step #8 to make a polymer preform.
10. Place the polymer preform from Step #9 into 85° C. shaker bath for 1 hour and then raise bath temperature to 95° C. and hold for another hour.

11. Filter and cool product dispersion.

The resulting encapsulated bioactive compound has a relatively narrow particle size distribution (by scanning electron microscopy, SEM). The particles were comparable to those obtained in Example 1.

Encapsulation and evaluation of an insecticide

Example 6

Encapsulation of 1H-Pyrazole-4-carboxylic acid, 3-(4-chlorophenyl)-4,5-dihydro-4-methyl-1-[[[4-(trifluoromethyl)phenyl]amino]carbonyl]-, methyl ester 1. In a Waring blender 1.85 parts of 10% 1H-Pyrazole-4-carboxylic acid, 3-(4-chlorophenyl)-4,5-dihydro-4-methyl-1-[[[4-(trifluoromethyl)phenyl]amino]carbonyl]-, methyl ester in alkylbenzenes based solvent (Aromatic 200, Exxon Corporation), 1.09 parts of monomer solution (75 parts of MMA, 25 parts of MAA, and 3.5 parts of t-BPO), 0.53 parts of DOSS (2% solution in water), 0.13 parts of methyl beta-cyclodextrin (50.8% solution in water, Wacker Company), and 2.05 parts of deionized water were emulsified at very high shear for 3 min.
2. To the emulsified mixture, was added 0.98 parts of an emulsion latex (29.76% polymer by weight, 0.562 micron particle size, poly(butyl acrylate/styrene/hexanethiol//82/18/19)). The emulsion mixture was then subject to mild agitation for 1 hour at room temperature.
3. The above mixture, which was 50% water, was diluted to 79% water by weight. The reaction mixture was added to a sealed pressure tube and subjected to mild agitation in a hot water bath at 85° C. for 1 hour and at 95° C. for 1 hour.
4. The mixture was cooled and sampled for optical microscopy. The sample was then dried and examined by SEM. Uniform sized particles of approximately 1.25 microns diameter were observed.

Example 7

Encapsulation of 1H-Pyrazole-4-carboxylic acid, 3-(4-chlorophenyl)-4,5-dihydro-4-methyl-1-[[[4-(trifluoromethyl)phenyl]amino]carbonyl]-, methyl ester (Higher Acid Shell)

1. In a Waring blender 2.11 parts of 10% 1H-Pyrazole-4-carboxylic acid, 3-(4-chlorophenyl)-4,5-dihydro-4-methyl-1-[[[4-(trifluoromethyl)phenyl]amino]carbonyl]-, methyl ester in alkylbenzenes solvent, 0.828 parts of monomer solution (55 parts of MMA, 45 parts of MAA, and 3.5 parts of t-BPO), 0.53 parts of DOSS (2% solution in water), 0.13 parts of methyl beta-cyclodextrin (50.8% solution in water, Wacker Company) and 2.04 parts of deionized water were emulsified at very high shear for 3 min.
2. To the emulsified mixture, was added 0.98 parts of an emulsion latex (29.76% polymer by weight, 0.562 micron particle size, poly(butyl acrylate/styrene/hexanethiol//82/18/19)). The emulsion mixture was then subject to mild agitation for 1 hour at room temperature.
3. The above mixture, which was 50% water, was diluted to 79% water by weight. The reaction mixture was added to a sealed pressure tube and subjected to mild agitation in a hot water bath at 85 C. for 1 hour and at 95 C. for 1 hour.
4. The mixture was cooled and sampled for optical microscopy. The sample was then dried and examined by SEM. Uniform sized particles of ~1.25 microns diameter were observed.

Preparation of a Comparison Emulsifiable Concentrate Sample 1. 0.5 parts of 1H-Pyrazole-4-carboxylic acid, 3-(4-chlorophenyl)-4,5-dihydro-4-methyl-1-[[[4-(trifluoromethyl)phenyl]amino]carbonyl]-, methyl ester was dissolved in 85 parts of alkylbenzenes solvent and mixed with 0.5 parts of Sponto™ 232-T and 0.5 parts of Sponto™ 234-T surfactants (Witco company).

Preparation of Comparison Encapsulation Blank Samples

The above procedures for preparation of Examples 5 and 6 were followed except that equal parts of alkylbenzene solvent were used in the place of the 10% 1H-Pyrazole-4-carboxylic acid, 3-(4-chlorophenyl)-4,5-dihydro-4-methyl-1-[[[4-(trifluoromethyl)phenyl]amino]carbonyl]-, methyl ester.

Evaluation of Insecticidal Activity

The encapsulated samples, control samples, and EC sample were diluted in water to make solutions at various concentrations of insecticide. Lima bean leaves were dipped in these solutions and allowed to dry and then fed to the larvae of southern army worm on petri dishes. There were 10 larvae per petri dish and two replicates per dose. The mortality of the larvae 6 days after feeding was recorded. The results are found in the following table.

| Concentration | % Mortality | | |
| --- | --- | --- | --- |
| ppm | EC | Ex. 6 | Ex. 7 |
| Blank | 0 | 0 | 0 |
| 0.072 | | 0 | |
| 0.10 | 0 | | |
| 0.13 | | | 0 |
| 0.22 | | 0 | |
| 0.30 | 55, 40* | | |
| 0.38 | | | 15 |
| 0.72 | | 0 | |
| 1.00 | 85, 45 | | |
| 1.27 | | | 25 |
| 2.15 | | 40 | |
| 3.00 | 100, 100 | | |
| 3.81 | | | 100 |
| 7.17 | | 100 | |
| 10.00 | 100, 100 | | |
| 12.69 | | | 100 |

*= Measurement taken in side-by-side comparison with Examples 6 and 7

These results indicate that the encapsulated insecticide may show similar biological activity as a standard emulsifiable concentrate formulation of the insecticide. Furthermore, the data also indicate that the insecticidal activity of the encapsulated sample improves as the content of acidic functionality in the encapsulating polymer increases. This can be explained by the fact that the armyworm gut is known to be alkaline.

We claim:

1. A method for administering a bioactive material, comprising:
    delivering to a target or the locus of the target a polymer encapsulated bioactive material comprising a polymer and a bioactive material selected from one or more of biocides, herbicides, mildewicides, insecticides, and fungicides, wherein:
    i) the particles of polymer encapsulated bioactive material have a particle size in the range of from 0.1 to 15 microns;
    ii) the particles of polymer encapsulated bioactive material have a particle size distribution, calculated by dividing the weight average size of the particles by the number average size of the particles of from 1.0 to 1.5;
    iii) the particles have a core/shell structure:
    iv) the polymer shell is not permeable to the bioactive material under ambient conditions and is at least partially permeable to the bioactive material at tho target; and v) in the process to form the polymer encapsulated bioactive material, the bioactive material is a liquid at the temperature at which swelling of seed polymer particles occurs and the bioactive material is a liquid at the temperature at which the polymerization forming the core/shell structure occurs; and wherein the polymer encapsulated bioactive material is prepared by:

i) a process comprising the steps of:
   a) combining an aqueous emulsion comprising the bioactive material with an aqueous emulsion of seed polymer particles;
   b) allowing the seed polymer particles to be swelled by the components of the emulsion comprising the bioactive material, forming swelled droplets;
   c) combining an aqueous emulsion comprising one or more monomer units derived from one or more of styrene, a-methylstyrene, vinyltoluene, vinyl acetate, ethylvinylbenzene, divinylbenzene, acrylonitrile, acrylic acid, methacrylic acid, amides of acrylic acid, alkyl esters of acrylic acid, allyl esters of acrylic acid, amine containing esters of acrylic acid, hydroxyalkyl esters of acrylic acid, amides of methacrylic acid, alkyl esters of methacrylic acid, amine containing esters of methacrylic acid, allyl esters of methacrylic acid, and hydroxyalkyl esters of methacrylic acid, and one or more initiators with the swelled droplets;
   d) further swelling the swelled droplets; and
   e) polymerizing the monomer, in the swelled droplets to form the polymer encapsulated bioactive material; or ii) a process comprising the steps of:
   a) combining an aqueous emulsion comprising the bioactive material, one or more monomer units derived from one or more of styrene, a-methylstyrene, vinyltoluene, vinyl acetate, ethylvinylbenzene, divinylbenzene, acrylonitrile, acrylic acid, methacrylic acid, amides of acrylic acid, alkyl ester, of acrylic acid, allyl esters of acrylic acid, amine containing esters of acrylic acid, hydroxyalkyl esters of acrylic acid, amides of methacrylic acid, alkyl esters of methacrylic acid, amine containing esters of methacrylic acid, allyl esters of methacrylic acid, and hydroxyalkyl esters of methacrylic acid, and one or more initiators with an aqueous emulsion of seed polymer particles;
   b) allowing the seed polymer particles to be swelled by the components of the emulsion comprising the bioactive material, one or more monomers, and one or more initiators, forming swelled droplets; and
   c) polymerizing the monomers in the swelled droplets to form the polymer encapsulated bioactive material.

2. The method of claim 1 wherein the bioactive material is dermally toxic.

3. The method of claim 1 wherein the polymer encapsulated bioactive material has a particle size distribution of from 1.0 to 1.3.

4. The method of claim 1 wherein the polymer encapsulated bioactive material has a particle size in the range of from 0.25 to 3 microns.

5. The method of claim 1 wherein the bioactive material is selected from herbicides and insecticides.

6. The method of claim 1 wherein the polymer comprises monomer units derived from one or more of methacrylic acid, methyl methacrylate, hydroxyethylmethacrylate, butyl acrylate, and styrene.

7. The method of claim 1 wherein the polymer has a glass transition temperature less than 50 decrees Celcius.

8. The method of claim 1 wherein the polymer comprises monomer units derived from methacrylic acid and at least one other monomer.

* * * * *